United States Patent
Kapadia

(10) Patent No.: US 9,301,838 B2
(45) Date of Patent: Apr. 5, 2016

(54) APPARATUS AND METHOD FOR DELIVERING A STRUCTURE TO A DESIRED TARGET SITE

(71) Applicant: THE CLEVELAND CLINIC FOUNDATION, Cleveland, OH (US)

(72) Inventor: Samir Kapadia, Chagrin Falls, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 14/190,324

(22) Filed: Feb. 26, 2014

(65) Prior Publication Data

US 2014/0243994 A1    Aug. 28, 2014

Related U.S. Application Data

(60) Provisional application No. 61/769,472, filed on Feb. 26, 2013.

(51) Int. Cl.
  *A61F 2/24* (2006.01)

(52) U.S. Cl.
  CPC ............... *A61F 2/243* (2013.01); *A61F 2/2439* (2013.01); *A61F 2/2466* (2013.01); *A61F 2220/0091* (2013.01); *A61F 2250/0096* (2013.01); *A61F 2250/0098* (2013.01)

(58) Field of Classification Search
  USPC ............ 623/1.1–1.26, 2.1–2.19, 23.68–23.71
  See application file for complete search history.

(56) References Cited

U.S. PATENT DOCUMENTS

| 2004/0148021 A1* | 7/2004 | Cartledge et al. ............ 623/2.37 |
| 2008/0167713 A1 | 7/2008 | Bolling |
| 2011/0313823 A1 | 12/2011 | Ikeuchi et al. |

FOREIGN PATENT DOCUMENTS

| EP | 2537487 A1 | 12/2012 |
| WO | 2004019826 A1 | 3/2004 |
| WO | 2010042950 A2 | 4/2010 |

OTHER PUBLICATIONS

PCT International Search Report and Written Opinion for PCT/US2014/018532, mailed Jun. 16, 2014, pp. 1-15.

* cited by examiner

*Primary Examiner* — Yashita Sharma
(74) *Attorney, Agent, or Firm* — Tarolli, Sundheim, Covell & Tummino LLP

(57) ABSTRACT

An apparatus for delivering an implanted structure to a desired target site within a body lumen of a patient includes a catheter having a longitudinally extending catheter lumen and adapted to provide access to the body lumen. A framing member has a collapsed condition in which the framing member is adapted for insertion into the body lumen through the catheter lumen and an expanded condition in which the framing member is adapted for placement within the body lumen. At least one target point is carried by the framing member and is adapted for placement adjacent the desired target site. A holding mechanism is carried by the framing member and is adapted to releasably grasp the implanted structure. At least one target pathway is attached to at least one target point. At least a portion of the target pathway extends through the catheter lumen.

14 Claims, 11 Drawing Sheets

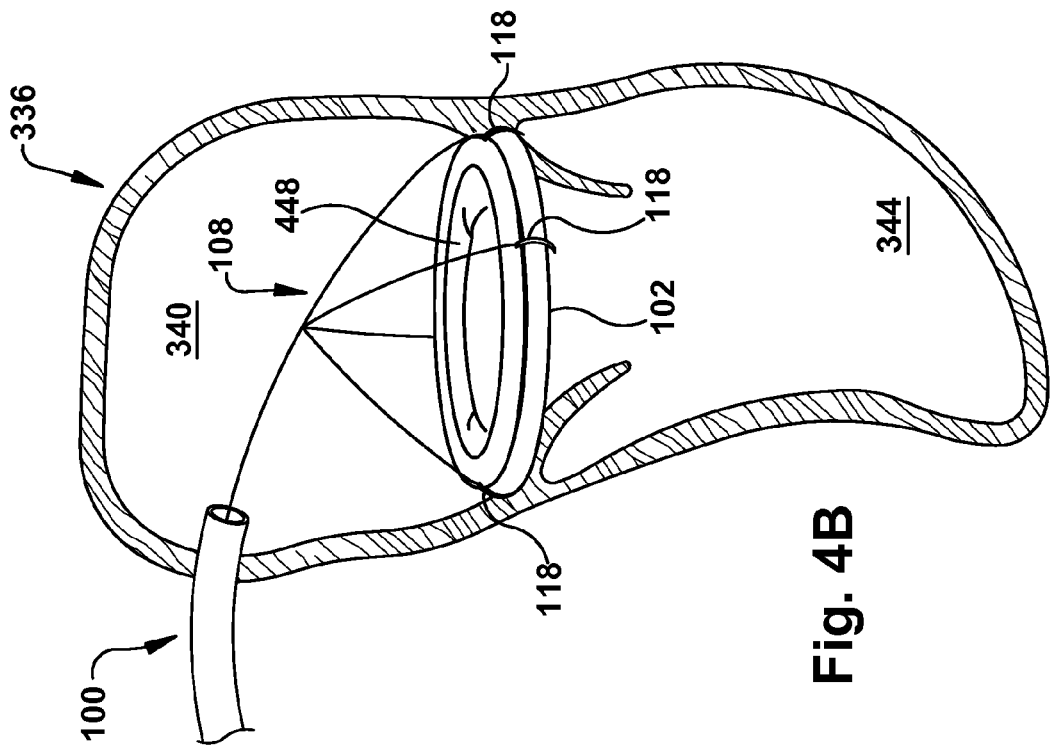
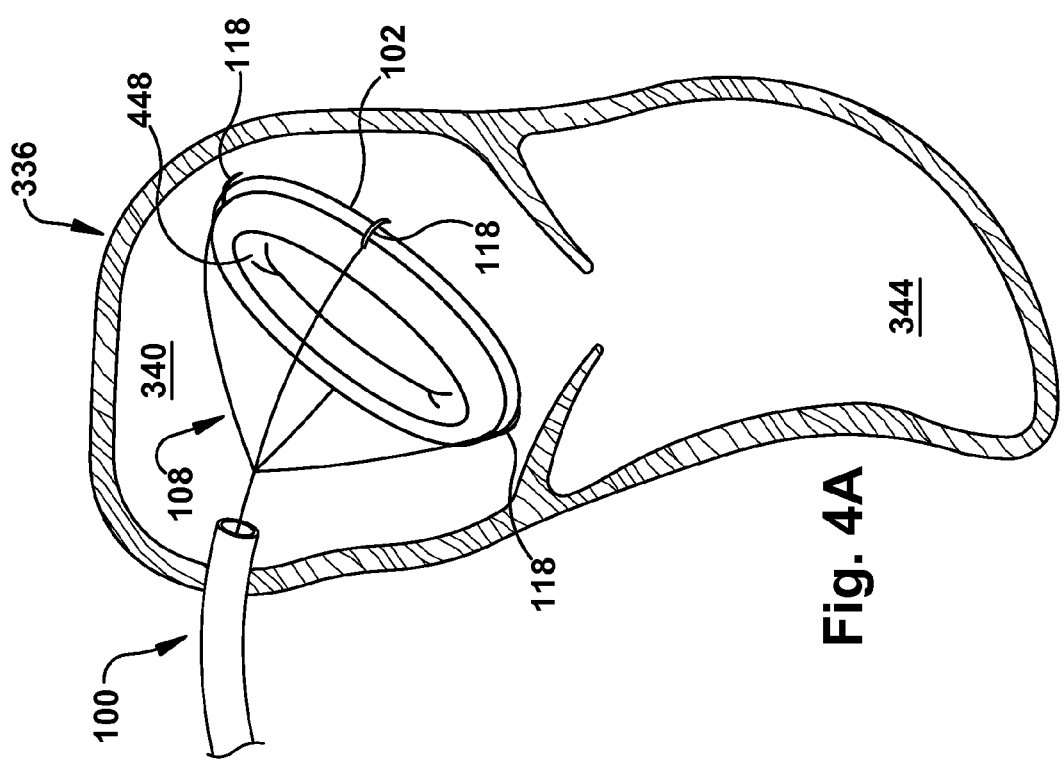

APPARATUS AND METHOD FOR DELIVERING A STRUCTURE TO A DESIRED TARGET SITE

RELATED APPLICATION

This application claims priority from U.S. Provisional Patent Application No. 61/769,472, filed 26 Feb. 2013, the subject matter of which is incorporated herein by reference in its entirety.

TECHNICAL FIELD

The present invention relates to an apparatus and method for delivering a structure to a desired target site and, more particularly, to a method and apparatus for delivering an implanted structure to a desired target site within a body lumen of a patient.

BACKGROUND OF THE INVENTION

It is known to implant prosthetic valves in various body lumens or passages to replace native valves that are diseased or otherwise defective in some manner. Blood pressure, as provided by heart activity via the arteries, is normally sufficient to maintain the flow of blood in one direction through the vasculature. The blood pressure in the veins is much lower than in the arteries and venous valves function to limit the backflow of blood through the veins. Numerous such venous valves are located throughout the venous system and are particularly important to maintaining directional blood flow in the lower extremities.

Venous valves can become incompetent and lead to chronic venous insufficiency. Various surgical techniques have been developed for treating incompetent venous valves including valvuloplasty, transplantation, and replacement with a prosthetic valve. These known surgical techniques include both open and percutaneous approaches. As with any prosthetic, compatibility issues for prosthetic venous valves are important, along with the need to avoid thrombosis and platelet deposition.

Another common type of prosthetic valve is a prosthetic cardiac valve. Prosthetic cardiac valves have been used to replace all four of the native cardiac valves. Cardiac valve replacement has traditionally been done though an invasive open surgical procedure, although endovascular (or percutaneous) approaches are increasingly being used.

The four native cardiac valves (mitral, aortic, tricuspid, and pulmonary) serve to direct the flow of blood through the two sides of the heart in a forward direction. On the left (systemic) side of the heart, the mitral valve is located between the left atrium and the left ventricle, while the aortic valve is located between the left ventricle and the aorta. These two valves direct oxygenated blood coming from the lungs, through the left side of the heart, into the aorta for distribution to the body. On the right (pulmonary) side of the heart, the tricuspid valve is located between the right atrium and the right ventricle, while the pulmonary valve is located between the right ventricle and the pulmonary artery. These two valves direct de-oxygenated blood coming from the body, through the right side of the heart, into the pulmonary artery for distribution to the lungs, where it again becomes re-oxygenated to begin the circuit anew.

All four of these native cardiac valves are passive structures that do not themselves expend any energy and do not perform any active contractile function. The valves consist of moveable leaflets that open and close in response to differential pressures on either side of the valve. The mitral and tricuspid valves are referred to as atrioventricular valves because they are situated between an atrium and a ventricle on each side of the heart. The mitral valve has two leaflets and the tricuspid valve has three leaflets. The aortic and pulmonary valves are referred to as semilunar valves because of the unique appearance of their leaflets, which are often termed "cusps" and which are shaped somewhat like a half-moon. The aortic and pulmonary valves each have three cusps.

Cardiac valves can exhibit abnormal anatomy and function as a result of congenital or acquired valve disease. Congenital valve abnormalities may be so severe that emergency surgery is required within the first few hours of life, or they may be well-tolerated for many years only to develop a life-threatening problem in an elderly patient. Acquired valve disease may result from causes such as rheumatic fever, degenerative disorders of the valve tissue, bacterial or fungal infections, and trauma.

The two major problems that can develop with cardiac valves are stenosis, in which a valve does not open properly, and insufficiency (also called regurgitation), in which a valve does not close properly. Stenosis and insufficiency may occur concomitantly in the same valve or in different valves. Both of these abnormalities increase the workload and stress placed on the heart. The severity of this increased stress on the heart, and the heart's ability to adapt to it, determine whether the abnormal valve will have to be surgically repaired or replaced.

In addition to stenosis and insufficiency of cardiac valves, surgery may also be required for certain types of bacterial or fungal infections in which the valve may continue to function normally, but nevertheless harbors an overgrowth of bacteria on the leaflets of the valve that may flake off (or embolize) and lodge downstream in a vital artery. If this occurs on the valves of the left side (i.e., the systemic circulation side) of the heart, embolization results in sudden loss of the blood supply to the affected body organ and immediate malfunction of that organ. The organ most commonly affected by such embolization is the brain, in which case the patient suffers a stroke. Thus, surgical replacement of either the mitral or the aortic valve may be necessary for this problem even though neither stenosis nor insufficiency of either valve is present.

If a cardiac valve must be replaced, there are currently several options available, and the choice of a particular type of prosthesis (i.e., artificial valve) depends on factors such as the location of the valve, the age and other specifics of the patient, and the surgeon's experiences and preferences. Available prostheses include mechanical valves, tissue valves, and homograft valves.

Mechanical valves include caged-ball valves, bi-leaflet valves, and tilting disk valves. The main advantage of mechanical valves is their long-term durability. Their main disadvantage is that they require the patient to take systemic anticoagulation drugs for the rest of his or her life, because of the propensity of mechanical valves to cause blood clots to form on them.

Tissue valves are typically constructed either by sewing the leaflets of porcine aortic valves to a stent (to hold the leaflets in proper position), or by constructing valve leaflets from porcine or bovine pericardial tissue and sewing them to a stent. The stents may be rigid or slightly flexible and are typically covered with a fabric, such as the material sold under the trademark DACRON™, and then attached to a sewing ring for fixation to the patient's native valve annulus. The porcine or bovine tissue is chemically treated to alleviate any antigenicity (i.e., to reduce the risk that the patient's body will reject the foreign tissue). Tissue valves may be used to replace any of the heart's four valves. The main advantage of tissue valves is that they do not cause blood clots to form as readily as do the mechanical valves, and therefore, they do not necessarily require systemic anticoagulation.

Homograft valves are harvested from human cadavers. Homograft valves are most commonly implanted in the aortic position, but are also occasionally implanted in the pulmonary position. Homograft valves are specially prepared and frozen in liquid nitrogen, where they are stored for later use. The advantage of aortic homograft valves is that they appear to be as durable as mechanical valves, but do not promote blood clot formation and therefore do not require anticoagulation. The main disadvantage of these valves is that they are not available in sufficient numbers to satisfy the needs of patients who need new aortic or pulmonary valves. Homograft valves are also extremely expensive and can be more difficult to implant than either mechanical valves or tissue valves.

Cardiac valve replacement using any of the aforementioned prostheses has traditionally been done via an open surgical technique in which the thoracic cavity is opened. This exacting operation requires use of a heart-lung machine for external circulation of the blood as the heart is stopped and opened during the surgical intervention and the artificial cardiac valve is implanted under direct vision. This operation exposes the patient to many risks, especially in the elderly population. Hence, an apparatus for repairing the function of a diseased cardiac or venous valve via an endovascular (or percutaneous) procedure, rather than an open surgical procedure, could offer tremendous benefits for these patients, many of whom have no options today.

In addition to the aforementioned venous and cardiac valves, it may be desirable to implant a ring (e.g., mitral valve reinforcement ring), an occluder, or any other type of prosthetic device or structure to a desired location within a patient's body.

SUMMARY OF THE INVENTION

In an embodiment of the present invention, an apparatus for delivering an implanted structure to a desired target site within a body lumen of a patient is described. A catheter has a longitudinally extending catheter lumen and is adapted to provide access to the body lumen. A framing member has a collapsed condition in which the framing member is adapted for insertion into the body lumen through the catheter lumen and an expanded condition in which the framing member is adapted for placement within the body lumen. The framing member has a framing member body. At least one target point is carried by the framing member and is adapted for placement adjacent the desired target site. A holding mechanism is carried by the framing member and is adapted to releasably grasp the implanted structure. At least one target pathway is attached to at least one target point. At least a portion of the target pathway extends through the catheter lumen.

In an embodiment of the present invention, a method for delivering an implanted structure to a desired target site within a body lumen of a patient is described. A catheter having a longitudinally extending catheter lumen is inserted into the patient. The catheter is advanced into a body lumen of the patient. A framing member is provided, the framing member having a framing member body and carrying at least one target point and a holding mechanism. The target point is adapted for placement within the body lumen to indicate the desired target site. The holding mechanism is adapted to releasably grasp the implanted structure. At least one target pathway attached to at least one target point is provided. At least a portion of the target pathway extends through the catheter lumen. The framing member is inserted in a collapsed condition, with the holding mechanism grasping the implanted structure, into the body lumen through the catheter lumen. The framing member is expanded into an expanded condition within the body lumen. A position of the framing member is adjusted to place the target point into a predetermined relationship with the target site to indicate that the framing member has achieved a desired deployment position relative to the desired target site. The implanted structure is released from the holding mechanism at the desired target site once the framing member is in the desired deployment position.

BRIEF DESCRIPTION OF THE DRAWINGS

For a better understanding of the invention, reference may be made to the accompanying drawings, in which:

FIGS. 4A-4B are schematic side views of an alternate configuration of the embodiment of FIG. 1 in a portion of the second use environment.

DESCRIPTION OF EMBODIMENTS

Figure 1:
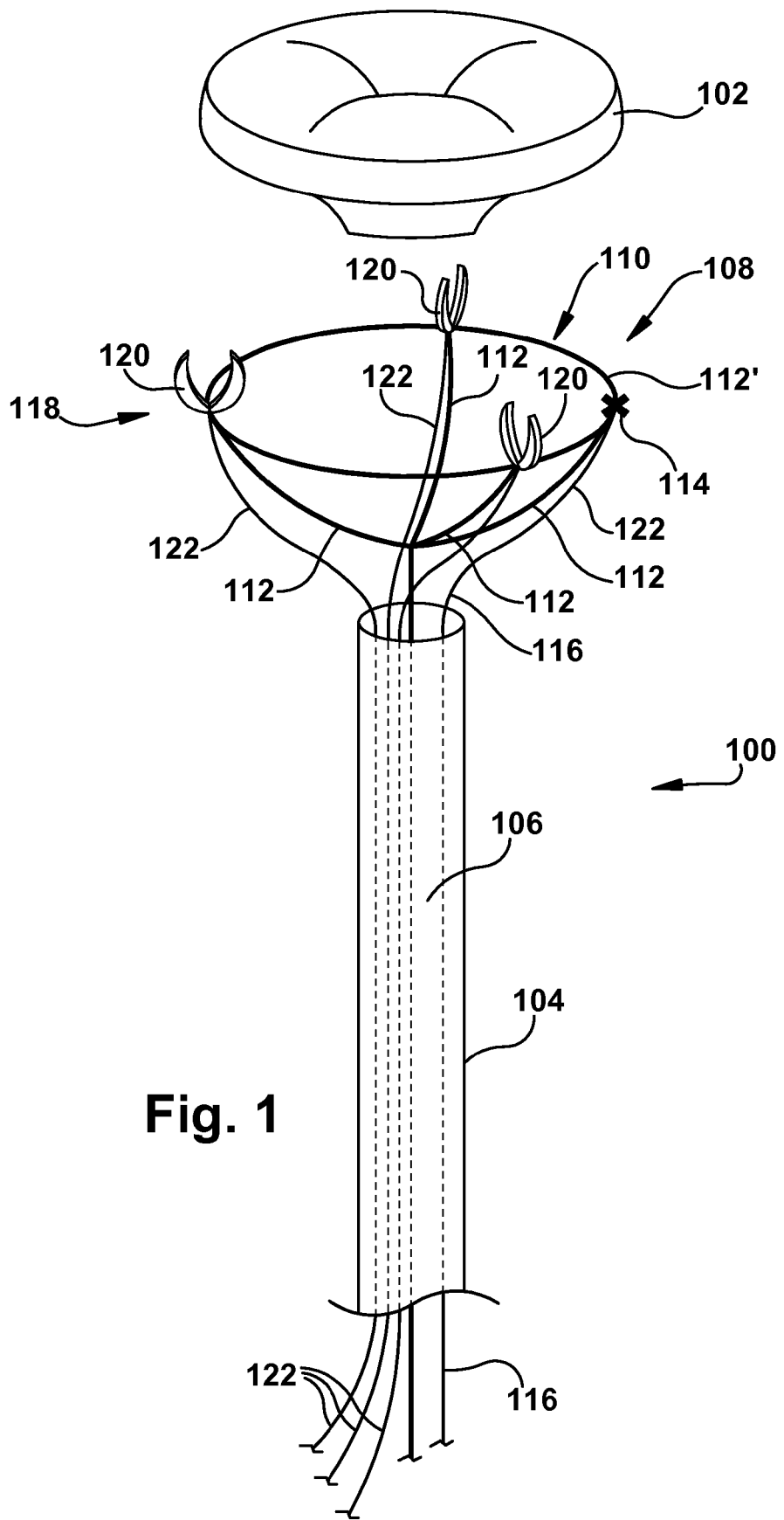
FIG. 1 is an exploded side view of one embodiment of the present invention.

In accordance with the present invention, FIG. 1 depicts a first embodiment of an apparatus 100 for delivering an implanted structure 102 to a desired target site within a body lumen of a patient. Throughout this description, the desired target site is presumed to be either a body lumen of any desired type or a valve location within a heart, but (as discussed below) may be any body tissue of a patient. Moreover, this description presumes that the desired target site is being targeted for delivery of an implanted structure 102. However, the apparatus 100 could be useful in precisely locating a desired target site which is being targeted for any reason, without limitation. For example, it may be useful to target a desired target site without altering the target site, for dissection/location/alignment of any body structure, for pinpointing a small branch from a blood vessel (i.e., targeting a void in a body tissue rather than a point on the body tissue), or the like. One of ordinary skill in the art could readily use the apparatus 100 for any application in which a target site is located for any reason or as a part of any procedure. However, for clarity, the below description presumes that the targeting is being accomplished as part of an implant-delivery procedure.

Similarly, the implanted structure 102, while shown in FIG. 1 as being a prosthetic valve, could be of any suitable type including, but not limited to, at least one of a ring, a valve, a suture, a graft, a pledget, an occluder device, an applicator of therapeutic means (e.g., light energy, heat energy, ultrasonic energy, a pharmaceutical substance, or the like), and a prosthesis of any desired type. The implanted structure 102 could be made of any type of natural or artificial materials and/or combinations thereof, including allograft, autograft, and homograft materials. The implanted structure 102 could be delivered to the target site for any reason and for any length of time, though it is contemplated that, for most applications of the present invention, at least a portion of the implanted structure will remain within the patient, at or near the target site, after conclusion of the surgical procedure in which the apparatus 100 is used. It is also contemplated that, for some embodiments of the present invention, the implanted structure 102 could be configured to transition between collapsed and expanded conditions, in any suitable manner as would be useful in the sequence described below.

The apparatus 100 includes a catheter 104 having a longitudinally extending catheter lumen 106 and adapted to provide access to the target site of the body lumen through any suitable entry point and method, such as arterial or venous access, direct port access to the heart, and/or through gastrointestinal or any other type of endoscopy.

A framing member 108 has a collapsed condition (shown in FIG. 2A, discussed below) in which the framing member is adapted for insertion into the blood vessel through the catheter lumen 106. The framing member 108 also has an expanded condition, shown in FIG. 1, in which the framing member is adapted for placement within the body lumen. The framing member 108 shown in FIG. 1 is a loop of thin, flexible wire having a framing member body 110 and may be made of any suitable material such as, for example, a woven, drawn, or otherwise formed strand of Nitinol, stainless steel, nylon, plastic, or any other material as desired. The framing member 108 may be radiopaque, in whole or part, to facilitate positioning within the body lumen as desired. The framing member 108 could be self-expanding and/or expandable via application of some suitable outside force influence (e.g., a balloon, not shown). For example, the framing member 108 could be made from a memory alloy having the resting configuration shown in FIG. 1 but selectively compressible into the catheter 104 for delivery to the target site. As shown in FIG. 1, the framing member body 110 could have a substantially "funnel" or hemispherical shape.

It is contemplated that a maximum dimension of the framing member body 110 could be chosen responsive to a selected internal dimension of the body lumen at/near the target site. For example, in the depiction of FIG. 1, the framing member body 110 includes at least a substantially hoop-shaped framing member strand 112' defining a maximum diameter at a "mouth" of the hemispherical shape shown—any number or configuration of framing member strands 112 could be provided as part of a framing member body 110, and they need not bear a physical resemblance to one another. When the body lumen has an interior body lumen surface (e.g., an inside of a blood vessel), the hoop-shaped framing member strand 112' can be adapted to exert positive pressure (e.g., a laterally-directed outward force) at a plurality of locations (e.g., a circumference of the blood vessel) on the interior body lumen surface to maintain a position of at least a portion of the framing member 108 within the body lumen.

The framing member 108 carries at least one target point 114 (one shown in FIG. 1). The target point 114 is adapted for placement into a predetermined relationship with, such as adjacent to, a desired target site. The target point 114 may have an associated radiopaque marker (not shown) or otherwise be visible to an external imaging system or other remote detection system (not shown) when located within the patient's body, for example, in order to help indicate a position of the target point relative to the body lumen. The target point 114 may be affixed, as shown in FIG. 1, to the framing member body 110 or some structure thereof. It should be noted that the desired target site need not precisely coincide with a desired body lumen location for the implanted structure 102, but that the desired target site may take into account an "offset" or spacing of the target point 114 with respect to the implanted structure during the installation/implantation process.

Each target point 114 may be attached to a target pathway, shown in the Figures as a target wire 116. At least a portion of the target pathway extends through the catheter lumen 106. The target pathway may be substantially spaced apart from the framing member body 110. That is, a majority of the target pathway (e.g., the target wire 116) may be separate from, and spaced (usually laterally) from the framing member body 110, though the relatively small portion of the target pathway which is attached to the target point 114 may be located adjacent to, or even in contact with, the framing member body 110 without destroying this "substantial spacing apart". The target pathway need not be coaxial with the framing member 108 for some use environments of the present invention.

The target pathway could also/instead include a target lumen (not shown), which could facilitate guidance of a needle, fluid, catheter, or other substance/structure from outside the patient's body directly toward the target point 114.

The target wire 116 shown in the Figures may extend through the catheter lumen 106 between an external power source (not shown) and the target point 114. The target wire 116 may selectively provide at least one of an electrical and a mechanical signal to the target point 114 to indicate a position of the target point within the body lumen. Such indication may be made in a visual manner, and/or may be made in cooperation with an external imaging or other remote detection system.

For example, the target wire 116 could transmit a mechanical vibration to the target point 114 from a mechanical automatic and/or manual source to cause the target point to move slightly. The external imaging system would detect such a motion and responsively indicate the location of the target point in relation to the target site on the internal body lumen surface or some other body tissue structure. As another example, the target wire 116 could carry an electrical current and cause the target point 114 to emit an electromagnetic signal having certain predetermined signal characteristics. The external imaging system then would detect the emitted signal and responsively indicate the location of the target point 114 within the body lumen.

A holding mechanism 118 is carried by the framing member 108 and is adapted to releasably grasp the implanted structure 102. For example, and as shown in FIG. 1, a plurality of pincers 120 could be pivotally connected to the hoop-type framing member strand 112', with each pincer being operatively connected to a pull-wire 122. In the depicted arrangement, the pincers 120 are each spring-biased closed and used to grasp the implanted structure 102, such as by pinching around a ring of the shown example prosthetic valve. The holding mechanism 118 should be configured to grasp the implanted structure 102 before the apparatus 100 is inserted into the patient's body and to maintain hold on that implanted structure while the apparatus 100 is manipulated to place the target point 114 near the desired target site. Once the target point 114 is in a desired position with respect to the target site (e.g., detected and/or achieved with the help of an external imaging device such as a fluoroscope), in the example arrangement shown in FIG. 1, the pull-wires 122 may be pulled or otherwise manipulated to cause the pincer 120 jaws to open, thus releasing the implanted structure 102 from the apparatus 100.

As another example, at least a portion (not shown) of the holding mechanism 118 could be frangible, with some structure configured for manipulation by the user (e.g., via a ripcord) to cause that portion of the holding mechanism to separate and release the implanted structure 102 from the apparatus 100.

The holding mechanism 118, regardless of design and operating mechanism, should be remotely operable to release the implanted structure 102 within the body lumen when the framing member 108 has achieved a desired deployment position relative to the desired target site, which may be determined/achieved through use of at least one target point 114 and/or target wire 116 as a positional reference for the apparatus 100.

Depending on how the holding mechanism 118 or other structures of the apparatus 100 are arranged and/or guided within the body lumen, the target point 114 may need to be calibrated or otherwise adjusted with respect to the desired target site. One of ordinary skill in the art can readily compensate for any offset distance between the target point 114 and the actual position of the holding mechanism 118 or implanted structure 102 which may be caused by the framing member 108, catheter 104, target wire 116, or any other structure of the apparatus 100.

The operation of an embodiment of the present invention is depicted in a first use environment, which is a generic body lumen use environment, in the sequence of FIGS. 2A-2D. First, the catheter 104 is inserted into the patient's body in any suitable manner such as, but not limited to, a vascular cut-down and/or natural orifice insertion, and guided through the patient's body as desired until a distal end 224 of the catheter 104 achieves a location within a body lumen 226 that is located relatively near to a target site 228 (shown schematically by asterisks in FIGS. 2A-2D). Through longitudinal motion of the catheter 104 (shown by the longitudinal directional arrow in FIG. 2A), the catheter then achieves the position shown in FIG. 2A.

Regardless of the manner and location in which the catheter 104 is guided into position within the body lumen 226, the framing member 108 may be inserted, in the first (collapsed) condition, into the body lumen through the catheter lumen 106. The collapsed framing member 108 may be inserted into the patient's body concurrently with the catheter 104 or may be at least partially inserted, such as by longitudinal advancement, into a catheter 104 which already has been at least partially inserted in the body lumen 226. The framing member 108, in the collapsed condition, need not protrude from the catheter lumen 106 within the body lumen 226, but may do so if desired. The holding mechanism 118 (omitted from FIGS. 2A-2D for clarity), which is collapsible with the framing member 108, should be already holding on to an implanted structure 102 (which also could be collapsed) when the framing member 108 is carried to a location near the target site 228 within the catheter 104. Optionally, a delivery catheter (not shown) may act as an outer sheath to help the insertion of both the catheter 104 and the framing member 108, along with their related structures, into the patient's body.

Once the distal end 224 of the catheter 104 is sufficiently proximate the target site 228, the apparatus 100 can be deployed from the catheter. Optionally, the catheter 104 may be inserted a relatively deep distance into the body lumen 226, and the framing member 108 may be maintained at that insertion depth within the body lumen. The catheter 104 may then be at least partially retracted from the body lumen 226, thus moving relative to the framing member 108 and unsheathing the framing member. Otherwise, the catheter 104 may be maintained at a relatively shallow insertion distance into the body lumen 226, as shown in FIGS. 2A-2D, and the framing member 108 may then be moved longitudinally into the body lumen, toward the right in the orientation of FIGS. 2A-2D, to emerge from the catheter.

Figure 2A:
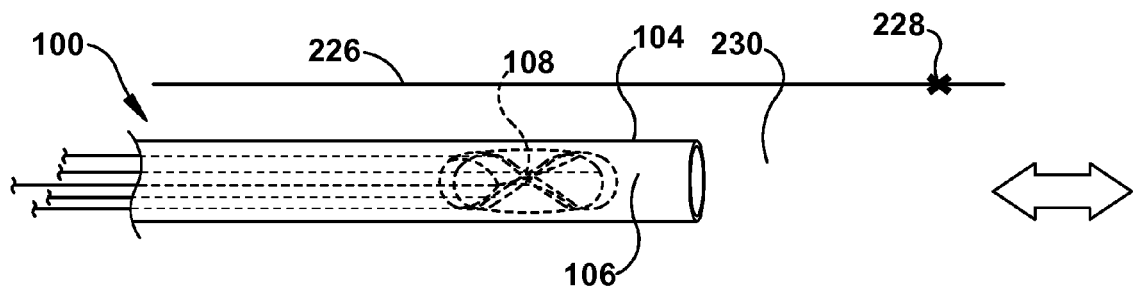
FIGS. 2A-2D are schematic side views of an example sequence of operation of the embodiment of FIG. 1 in a first use environment.
Figure 2B:
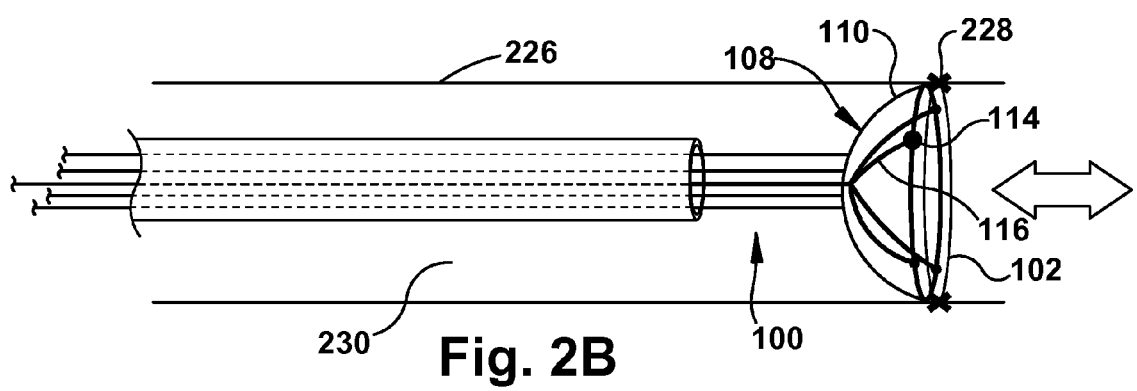

The framing member 108 is then expanded into the second (expanded) condition within the body lumen 226, as shown in the sequence from FIG. 2A to FIG. 2B. This expansion may be done in whole or in part, and as quickly as desired, depending upon the particular application of the apparatus 100. As mentioned above, the framing member 108 as shown in the Figures is a type that self-expands into the expanded condition.

As the framing member body 110 is brought into position within the body lumen 226 as desired near the target site 228, the framing member 108 may be manipulated to position the target point 114 adjacent an interior body lumen surface 230. Only one target point 114 is shown in FIGS. 2A-2D, for clarity. Optionally, the target point 114, the framing member 108, or some other structure of the apparatus 100 may contact the interior body lumen surface 230 before, during, and/or after positioning of the target point 114 in a desired relationship with the target site 228. The location of the target point 114 on the framing member 108 should be predetermined to facilitate positioning of the target point 114 as desired.

Optionally, the target point 114 may be slidably fastened to, or otherwise movable with respect to, the framing member 108. In such case, the target wire 116, when present, may assist in moving the target point 114 along the framing member 108 and into the desired position adjacent the body lumen 226.

Figure 2C:
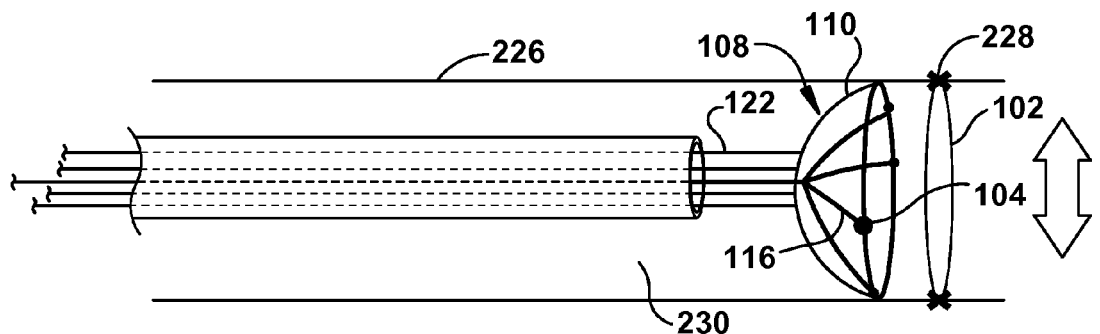

As shown in the sequence of FIG. 2B to FIG. 2C, the framing member 108 has been moved longitudinally (shown by the directional arrow of FIG. 2B) relative to the catheter 104. As is shown at least by the changed position of the target point 114 from FIG. 2B to FIG. 2C, the framing member 108 may also have been rotated laterally relative to the catheter 104, as shown by the directional arrow of FIG. 2C.

An external imaging system (not shown) may be used to detect the position of the target point 114 (such as in the longitudinally correct but laterally offset position from the target site 228 in FIG. 2B) and then provide the user with the information needed to guide manipulation of the framing member 108 (such as in the rotation or other lateral movement from FIG. 2B to FIG. 2C) to place the target point 114 as desired. The position may be established and viewed passively when the target point 114 includes a radiopaque or other marker.

Alternately, an active determination of the position of the target point 114 may be made, such as by selectively providing at least one of an electrical and a mechanical signal through the target wire 116 to the target point 114. An external imaging or other remote detection system may be used to sense a position-indication motion or signal produced by the target point 114 responsive to the electrical and/or mechanical signal. The user can then review the output of the remote detection system to determine the location of the target point 114 within the body lumen 226. This position-checking process may be repeated as needed at any suitable time throughout the targeting procedure.

When the framing member 108 has been expanded into the body lumen 226 and arranged as desired to bring the target point 114 into the desired position adjacent the target site 228, at least a portion of the framing member body 110 may lie in contact with the interior body lumen surface 230. That is, the framing member 108 may contact one or more locations on, or areas of, the interior body lumen surface 230.

The framing member 108 may exert a positive pressure on any areas of the interior body lumen surface 230 when in the expanded condition. The framing member 108 is optionally designed to brace against areas of the interior body lumen surface 230 (which could be remote from the target site 228) in order to maintain contact between the target point 114 and the interior body lumen surface. For instance, the framing member 108 may be designed to be slightly larger than the interior body lumen surface 230 in one or more dimensions when in the expanded condition, in order to exert a positive pressure needed to maintain the target point 114 in a desired position.

Once the target point 114 has been determined to be in a desired deployment position with respect to the target site 228 (either two- or three-dimensionally relative), the implanted structure 102 can be released from the holding mechanism 118 at the desired target site 228 and/or at a predetermined offset from the desired target site, depending on the nature of the physical relationship between the desired target site, the target point, and the implanted structure for a particular application of the present invention. For example, and for the apparatus 100 shown in FIG. 1, the pull wires 122 can be manipulated to open the pincers 120 and allow the implanted structure 102 to separate from the apparatus under body fluid, supplied fluid, gravitational, mechanical, magnetic, or any other motive separation power operative to urge the implanted structure away from the framing member 108.

Before, during, and/or after release from the implanted structure 102 within the body lumen 226 as desired, the implanted structure 102 could be secured to the body lumen (e.g., to an interior body lumen surface 230). This securement could occur manually and/or automatically, and using any desired mechanical (e.g., suture, staple, clip, or any other fastener), chemical (e.g., adhesive), or electrical (e.g. cautery) means, or any combination thereof.

Figure 2D:
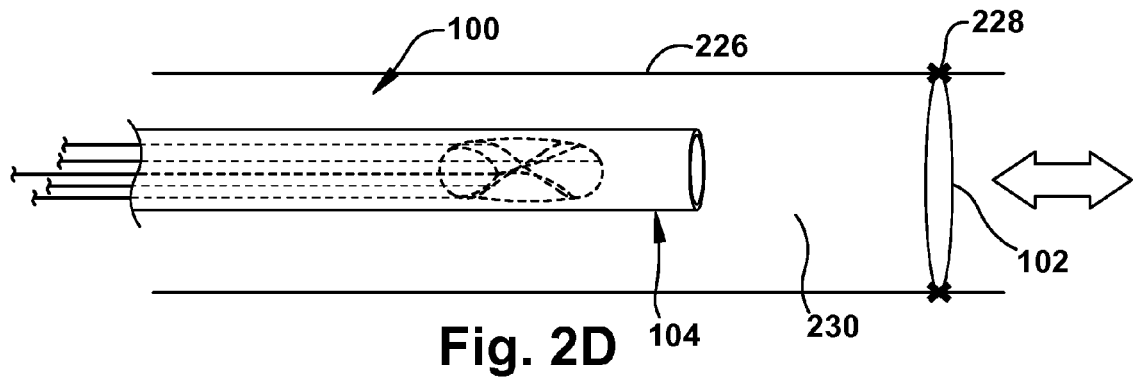

The apparatus 100, or portions thereof, may be removed from the body lumen 226 if desired, by reversing all or part of the above process. For example, and as shown in FIG. 2D, the framing member 108 (here along with the holding mechanism 118, target point 114, and target wire 116) can be collapsed and withdrawn longitudinally (in the direction of the arrow in FIG. 2D) into the catheter lumen 106. The catheter 104 can then be longitudinally withdrawn from the body lumen 226 concurrently with, or after, the collapsed framing member 108 and related structures of the apparatus 100 being withdrawn from the body lumen. The implanted structure 102 can be maintained at the desired target site 228 (or, when there is some offset built into the apparatus 100, at an installation site having a predetermined relationship with the desired target site) after the framing member 108 is withdrawn from the body lumen 226.

FIGS. 3A-3G illustrate the embodiment of FIG. 1 in a second use environment, which is a heart use environment. Description of common elements and operation similar to those in the previously described first use environment will not be repeated with respect to the second use environment.

Figure 3A:
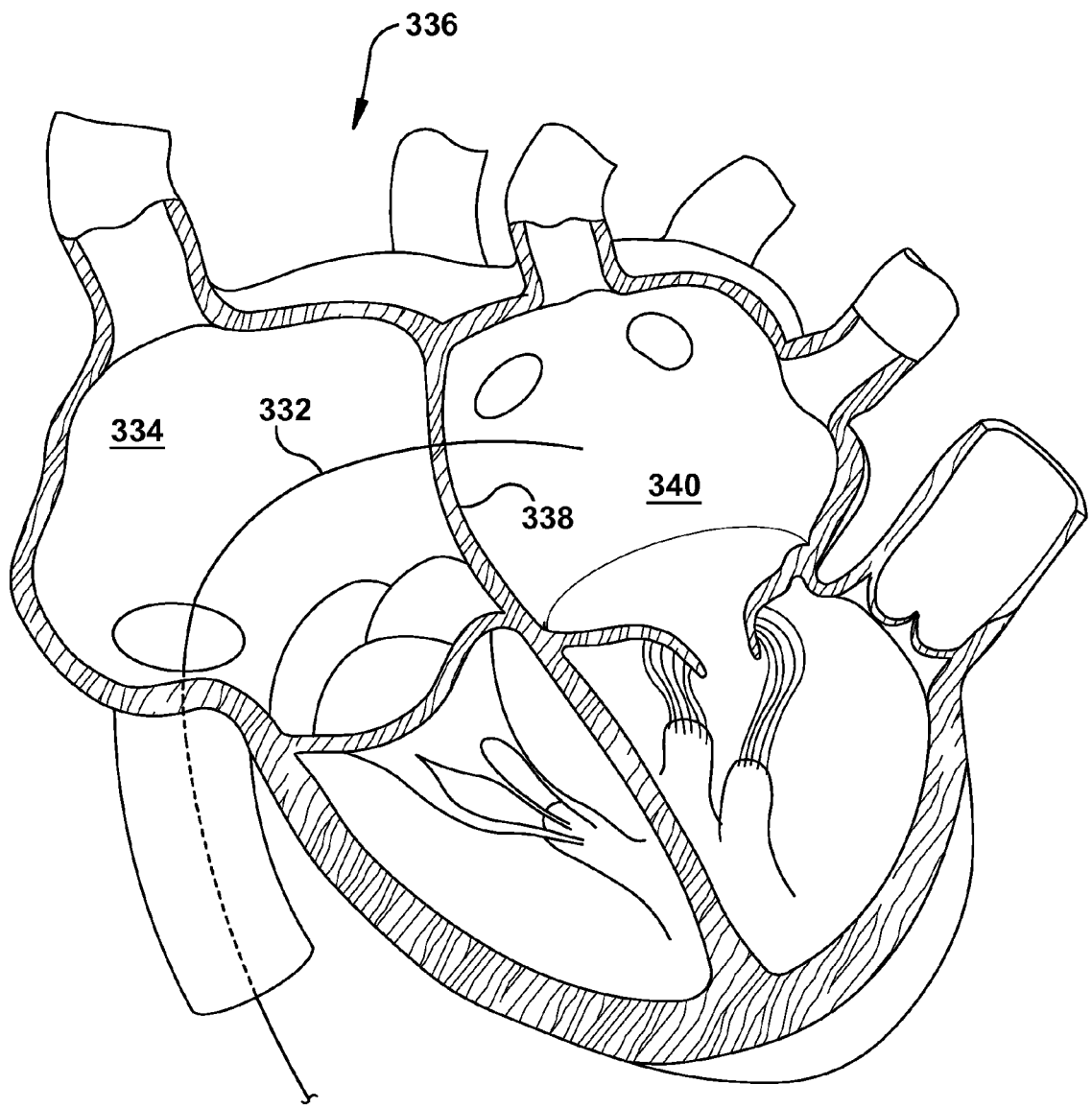
FIGS. 3A-3G are schematic side views of an example sequence of operation of the embodiment of FIG. 1 in a second use environment.
Figure 3B:
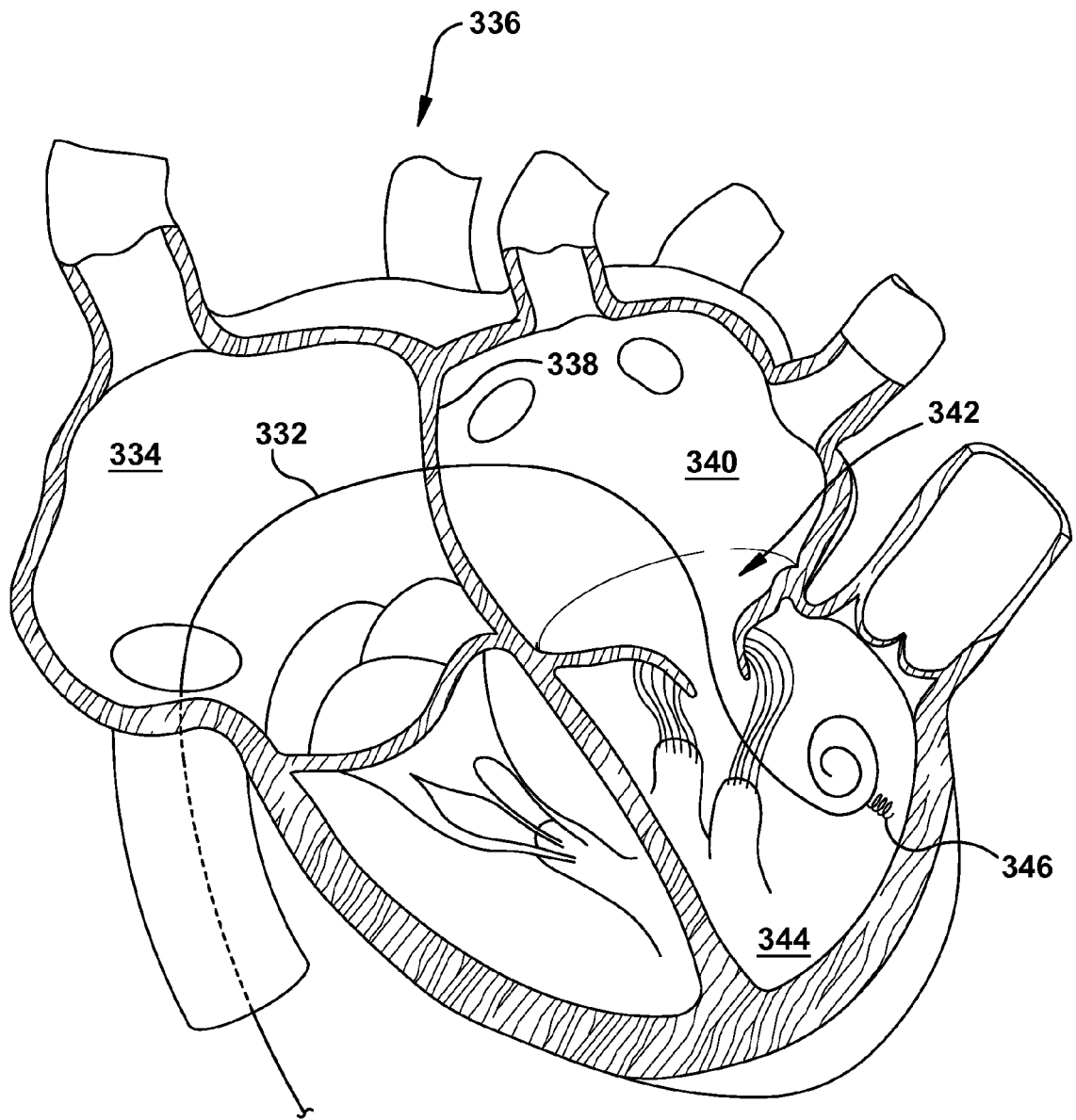

In this use environment, and as shown in the sequence of FIGS. 3A-3B, a guidewire 332 may be directed into a right atrium 334 of the heart 336 and guided through the interatrial septum 338 into the left atrium 340 in any desired manner. The guidewire 332 shown in FIG. 3B extends through the mitral valve 342 and into the left ventricle 344. Here, the combination of the left atrium 340, mitral valve 342, and left ventricle 344 are collectively functioning as a body lumen 226, with an annulus of the mitral valve being the target site.

Optionally, and as shown schematically by anchor 346 in FIG. 3B, a stabilized wire loop, screw-type structure, or any other suitable feature could be provided to the guidewire 332 or any desired structure of the apparatus 100 to help anchor at least a portion of the apparatus with respect to the heart 336 or other patient tissue having a predetermined relationship with the target site 228 for at least a portion of the time before, during, and/or after use of the apparatus 100 within the patient's body.

Figure 3C:
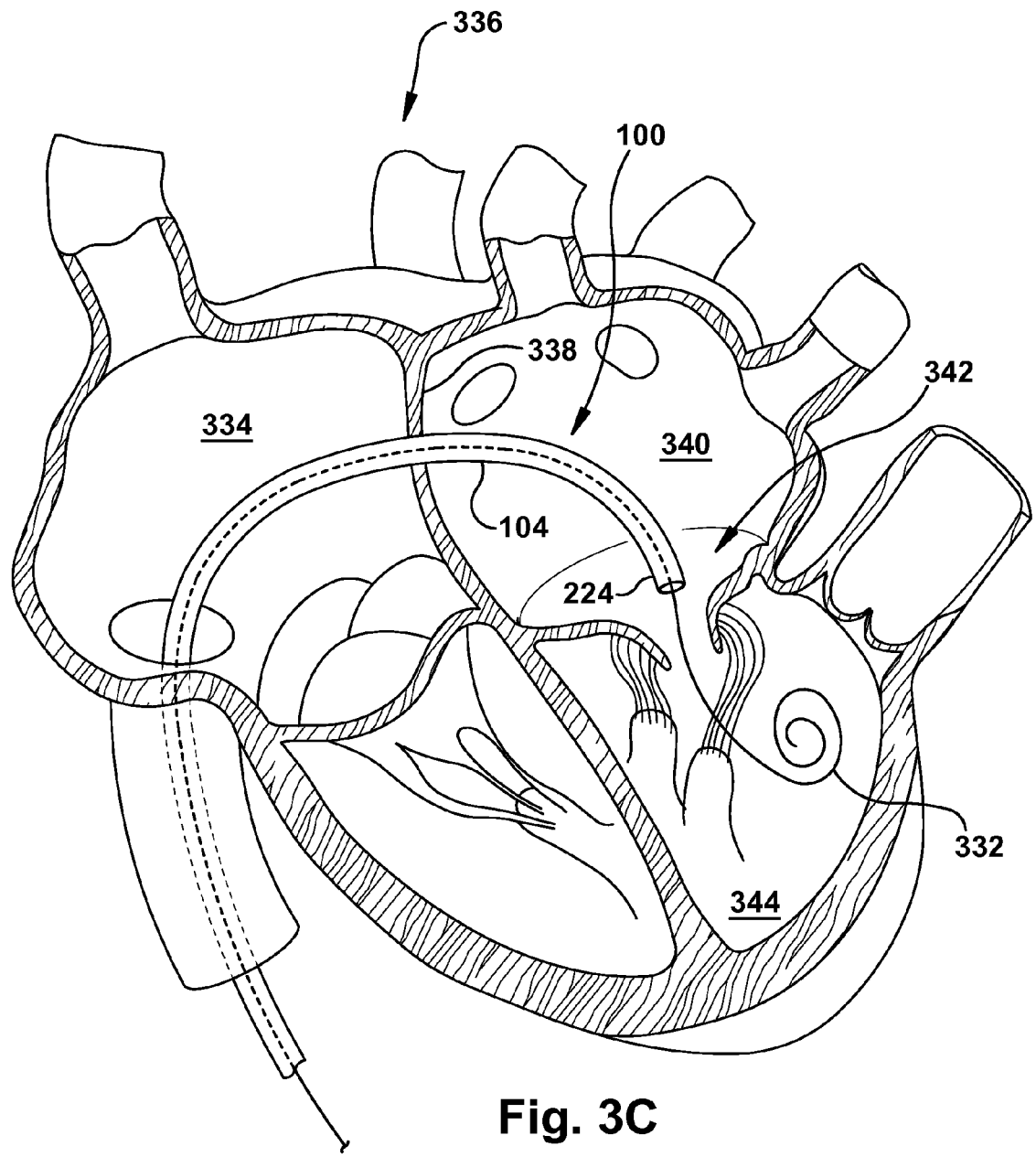

In FIG. 3C, the catheter 104 is inserted over the guidewire 332 until the distal end 224 of the catheter is adjacent the mitral valve 342 annulus.

Figure 3D:
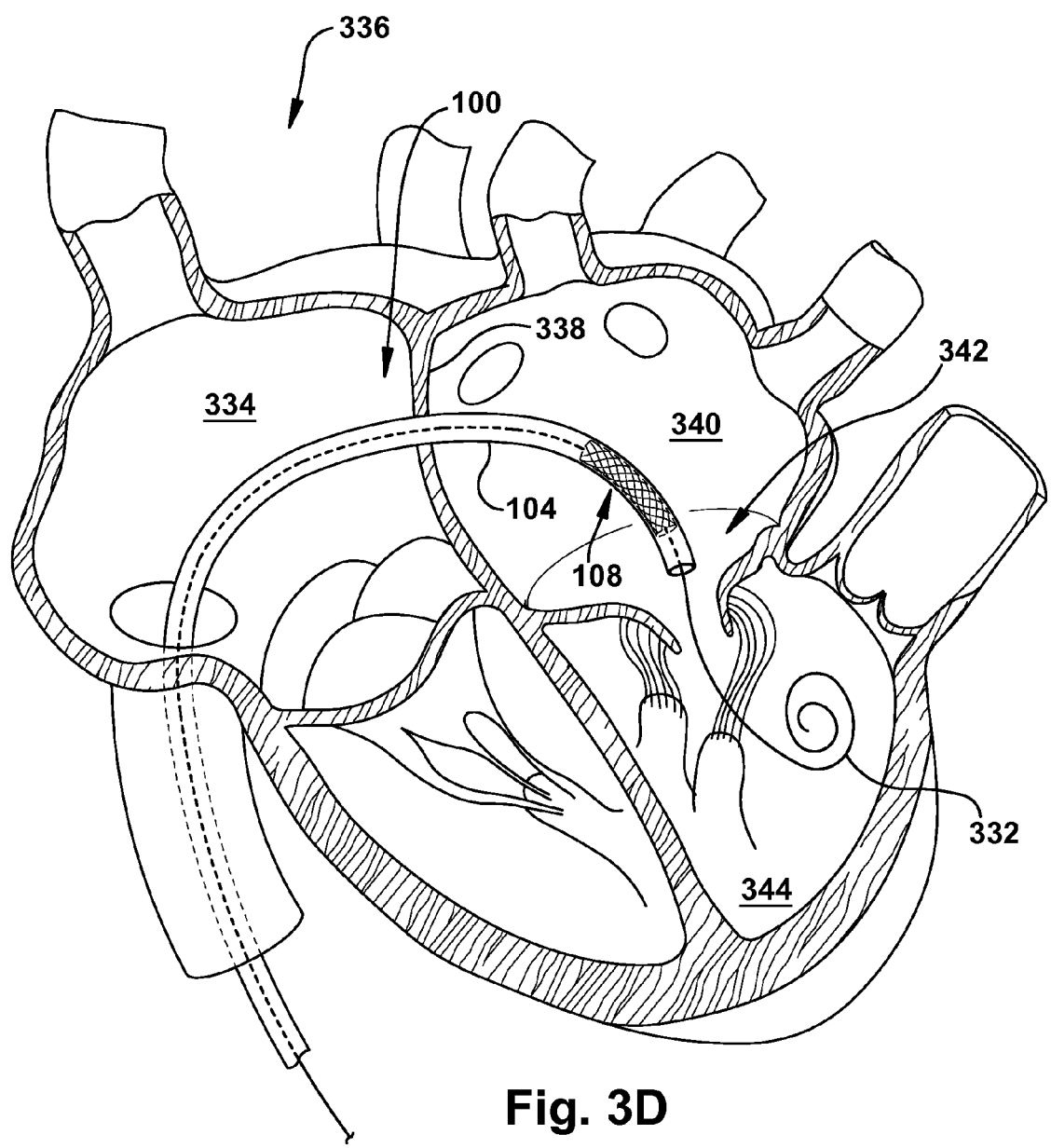

FIG. 3D shows insertion of the collapsed framing member 108, holding a collapsed implanted structure 102 (here, a mitral valve ring), through the catheter lumen 106.

Figure 3E:
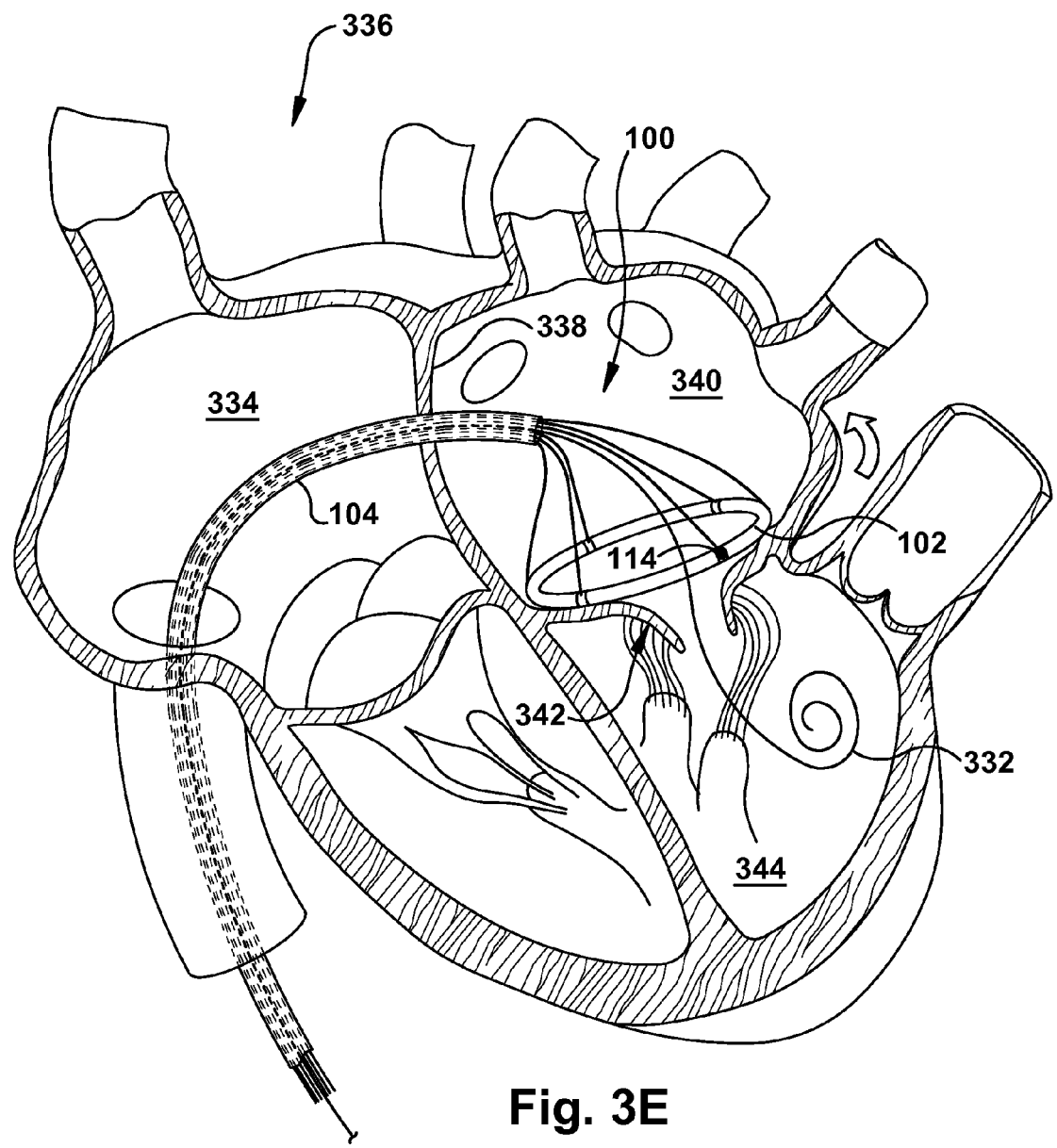

In FIG. 3E, the catheter 104 has been retracted slightly to facilitate expansion of the framing member 108, along with the retained implanted structure 102, at the annulus of the mitral valve 342. As is indicated by the directional arrow in FIG. 3E, the target point 114 must be rotated into the plane of the drawing (in the orientation of FIG. 3E) to achieve desired placement adjacent and/or contacting the mitral valve 342 annulus.

Figure 3F:
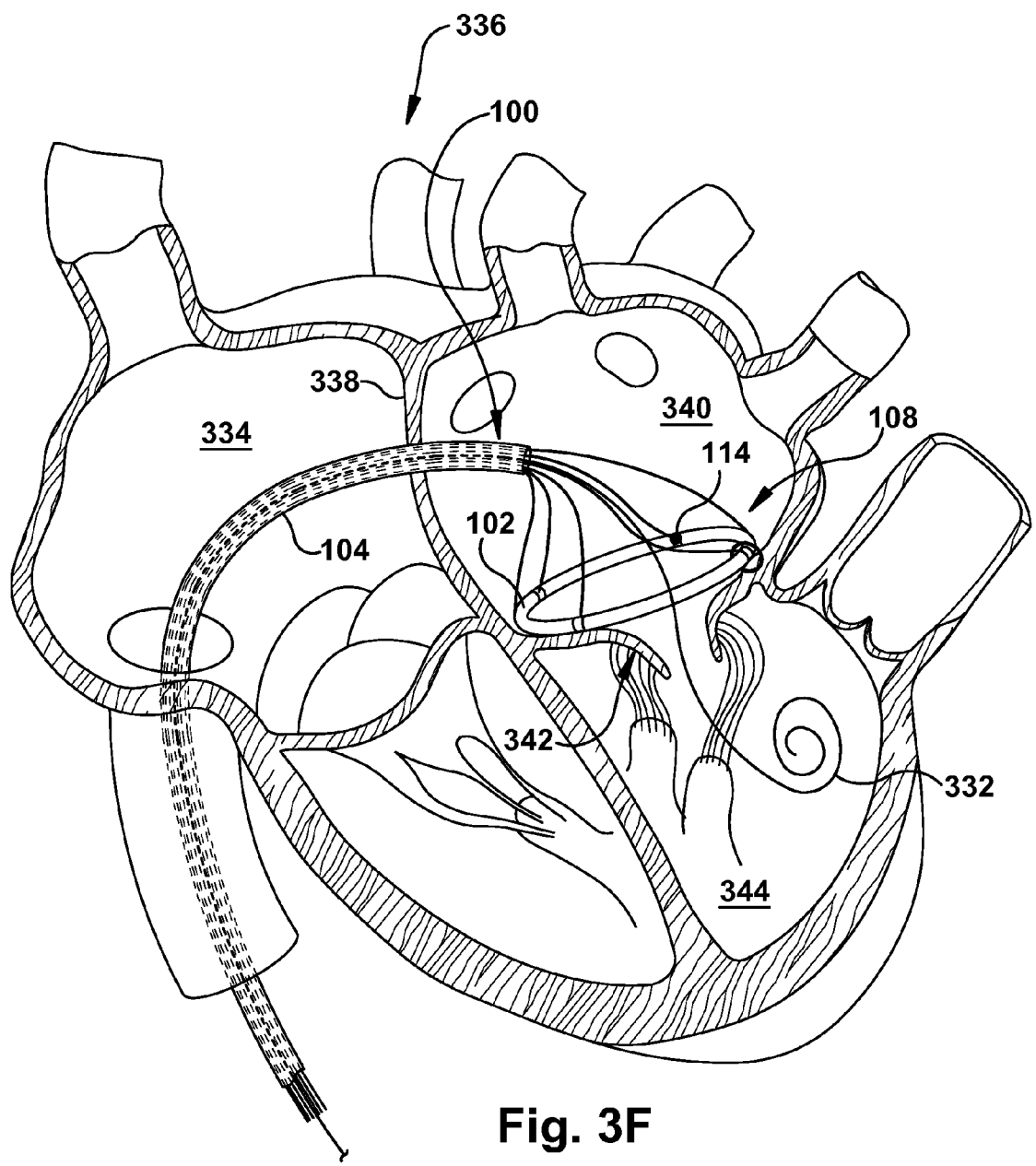

FIG. 3F shows the target point 114 rotated into the desired position with respect to the target site (the mitral valve 342 annulus). In the sequence from FIG. 3F to 3G, the holding mechanism 118 has been actuated to release the implanted structure 102 at the mitral valve 342 annulus. Though not shown, it is contemplated that sutures or staples could be installed, or any other securement means used, to temporarily and/or permanently affix the implanted structure 102 to the mitral valve 342 annulus before, during, and/or after release of the implanted structure 102 from the holding mechanism 118.

Figure 3G:
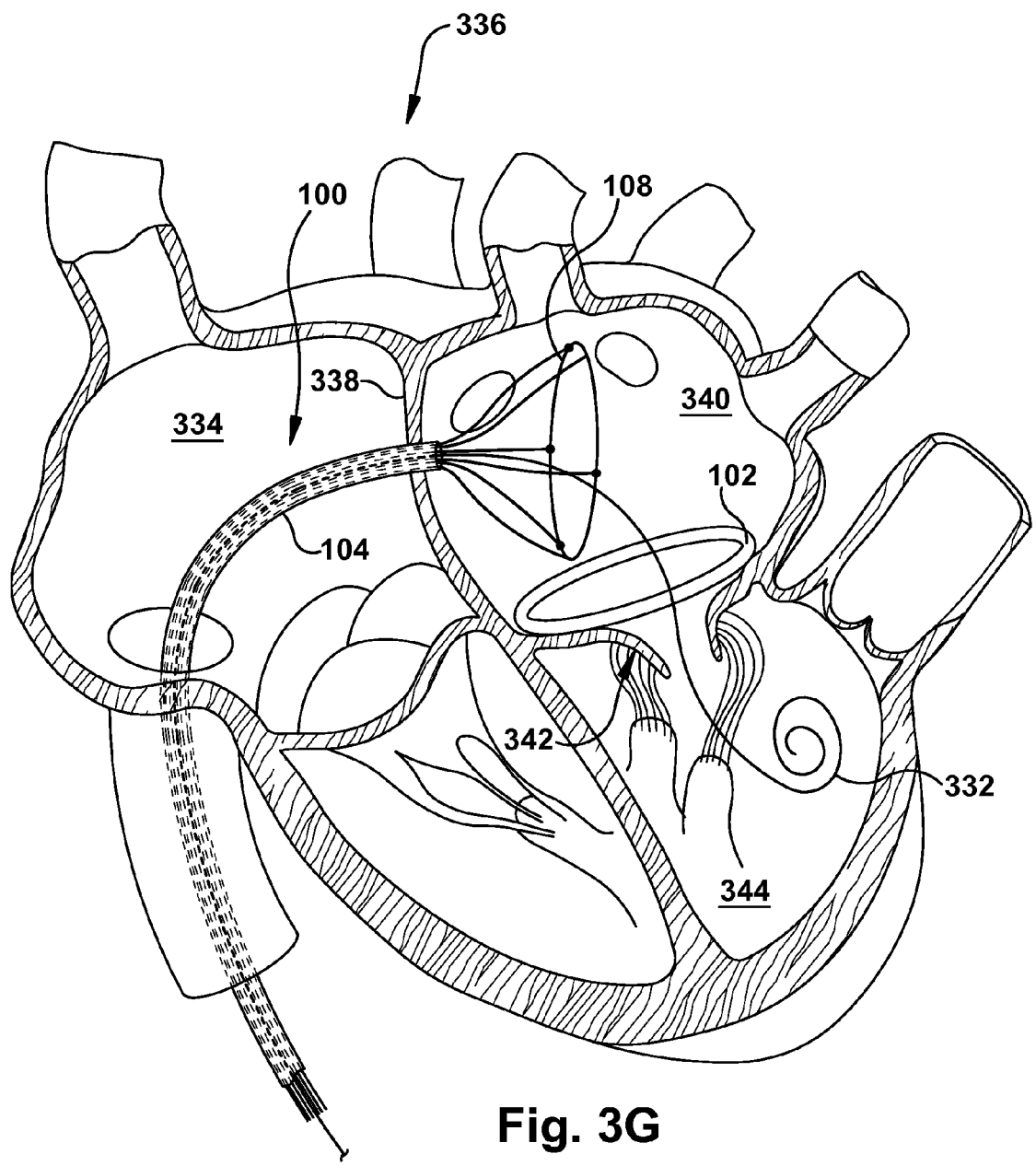

As shown in FIG. 3G, the framing member 108 has been retracted from the now-released implanted structure 102. The framing member 108 can now be collapsed back into the catheter 104 and removed from the heart 336 in any desired manner.

FIGS. 4A-4B illustrate an example configuration of the apparatus 100 in a portion of the second (heart) use environment. In FIG. 4A, the framing member 108 includes a temporary valve 448, in addition to the implanted structure 102 (shown here as an annular ring). As shown in FIG. 4A, the temporary valve 448 acts as a portion of the framing member 108, and is collapsible for insertion through the catheter lumen 106 along with the framing member. The temporary valve 448 can be placed, in the heart 336 environment, in a valve annulus (of any suitable valve, though shown here as a mitral valve 342), as shown in FIG. 4B. The temporary valve 448, when present, may assist with providing the user with an opportunity to secure the ring or other implanted structure 102 at/near the target site 228 (similar to the sequence of FIGS. 3A-3G) while maintaining heart 336 function during a beating-heart surgical procedure.

Figure 5:
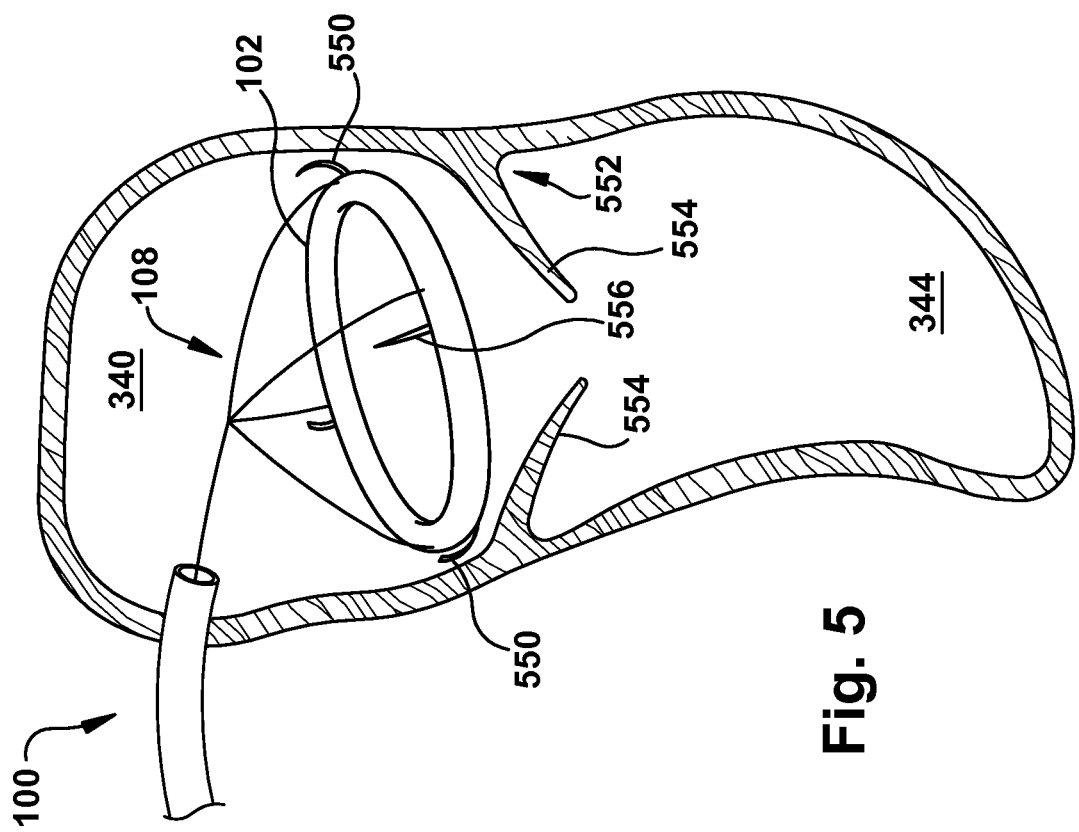
FIG. 5 is a schematic side view showing components of the embodiment of FIG. 1 in a portion of the second use environment.

FIG. 5 depicts additional features which can be provided to the apparatus 100 as desired for a particular use environment and/or surgical task being performed in that use environment. One or more locator structures (shown in FIG. 5 as hooks 550) may extend from some structure of the framing member 108 to assist with placement/location of the framing member during operation of the apparatus 100.

The locator structures may be configured to assist the user with longitudinal spacing of the implanted structure 102, such as by "catching" of the depicted hooks 550 on a predetermined patient tissue structure (e.g., a valve annulus 552). In the depicted configuration, a length, placement, or other physical property of the hooks 550 may serve to space the implanted structure 102 a predetermined distance above the valve annulus 552 when the hooks are "caught" on the valve annulus.

The hooks 550 or other locator structures may also function, in the configuration of FIG. 5, to flatten the native valve leaflets 554 against the adjacent heart wall and thus "pin" those native leaflets out of the way, temporarily or permanently, as desired for a particular implanted structure 102 and/or surgical procedure.

One or more attachment assisters, such as the needle 556 shown in FIG. 5, may be provided to the apparatus 100 to assist with attachment of the implanted structure 102 to the patient tissue. The attachment assisters could be similar to structures described in copending U.S. patent application Ser. No. 13/206,639, filed 10 Aug. 2011 and titled "Apparatus and Method for Targeting a Body Tissue" (now U.S. Patent Application Publication No. 2011/0313283), the entire contents of which are incorporated herein by reference. For example, the needle 556 and/or a stapler (not shown) could be operated remotely to pass a suture thread through the implanted structure 102 and the patient tissue to attach the two together. It is also contemplated that a suture thread (not shown) itself could serve as an implanted structure 102 and remain behind (e.g., when used to remodel a valve annulus 552) when the framing member 108 and other portions of the apparatus 100 are removed from the patient's body.

Though cardiovascular applications and environments of the apparatus 100 are given as examples above, it is contemplated that the present invention may be used in any medical application (for example, insertion through the mouth/esophagus and assisting with a bariatric surgical procedure), or even nonmedical applications (for example, insertion through a plumbing conduit and installation of an internal valve), as appropriate; any procedure requiring relatively precise location of a target site for delivery of an implanted structure could be a suitable environment for use of the present invention. For example, body cavities with which the apparatus 100 can be used include, but are not limited to, at least one of a left atrium, a right atrium, an interatrial septum, an interventricular septum, a peritoneal cavity, a chest cavity, a left atrial appendage, a right atrial appendage, a left pulmonary vein, a blood vessel, a common iliac artery, a subintimal space, a portion of the heart, a gastrointestinal organ, a genitourinary organ, a space external to the patient's body, and the like. Similarly, the body tissue associated with a body lumen may be, but is not limited to, at least one of an interatrial septum, a left atrial appendage wall, a right atrial appendage wall, a left pulmonary vein wall, a chest wall, an abdominal wall, a heart wall, a blood vessel wall, a common iliac artery wall, a gastrointestinal organ wall, a genitourinary organ wall, a skin of the patient, and the like. Indeed, the delivery of an implanted structure 102 need not always be the end result of using the present invention—the apparatus 100 could be applied instead, as discussed throughout, to simply precisely locate (and optionally mark) a specific area within a difficult-to-access structure.

It is also contemplated that, though the apparatus 100 is described as extending, in some example use environments, from an internal body location all the way outside the patient's body, a second catheter, guidewire, trocar, stent, or the like (not shown) could be used to enter the patient's body from externally in any manner, and at least a portion of the apparatus 100 could be linked with that second catheter, guidewire, trocar, stent, or the like inside the patient's body. In this manner, the apparatus 100 can assist in placing the internal structure in communication with an external structure, while the apparatus 100, or portions thereof, does not actually exit the patient's body.

Various aspects of the present invention may bear some resemblance to structures, functions, or other features discussed in U.S. Pat. No. 8,019,404, issued 13 Sep. 2011 and/or U.S. Patent Application Publication No. 2011/0313283, published 22 Dec. 2011, both by Samir Kapadia, both entitled "Apparatus and Method for Targeting a Body Tissue", and the subject matter of both of which is incorporated by reference herein in its entirety.

While aspects of the present invention have been particularly shown and described with reference to the preferred embodiment above, it will be understood by those of ordinary skill in the art that various additional embodiments may be contemplated without departing from the spirit and scope of the present invention. For example, the framing member 108, or the framing strands 110 thereof, may have any suitable shape, cross-sectional or otherwise (e.g., the framing member could have a generally tubular aspect provided by loops of framing strands or could resemble a conventional stent). The framing member 108, or the framing strands 110 thereof, may self-expand through the use of memory alloy materials, magnetic attraction/repulsion, or any other desired mechanism. The functions of the framing strands 110 and target wires 116 may be combined in a single structure. A wireless system may selectively provide an electrical signal to the target points 114 similarly to the target wire 116 system. The plurality of target points 114, when present, need not be matched in shape, size, attachment method, conductivity, or any other property. The catheter 104 may follow the framing member 108 through the body tissue during release of the implanted structure 102, or the catheter 104 may remain within the body lumen 226. Only one apparatus 100 is shown as being present in the embodiments described and shown herein, but any number of apparatus 100 may be used at a time, as desired for a particular application of the present invention. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, I claim:

1. An apparatus for delivering an implanted structure to a desired target site within a body lumen of a patient, the apparatus comprising:
   a catheter having a longitudinally extending catheter lumen and adapted to provide access to the body lumen;
   a framing member having a collapsed condition in which the framing member is adapted for insertion into the body lumen through the catheter lumen and an expanded condition in which the framing member is adapted for placement within the body lumen, the framing member having a framing member body;
   at least one target point carried by the framing member and adapted for placement adjacent the desired target site;
   a holding mechanism carried by the framing member and adapted to releasably grasp the implanted structure, the holding mechanism comprising a plurality of pincers pivotally connected to the framing member, with each pincer being operatively connected to a pull-wire; and
   at least one target pathway attached to at least one target point, at least a portion of the target pathway extending through the catheter lumen.

2. The apparatus of claim 1, wherein the target pathway extends between an external power source and the target point and selectively provides at least one of an electrical and a mechanical signal to the target point to indicate a position of the target point relative to the body lumen in cooperation with the external imaging system.

3. The apparatus of claim 1, wherein the framing member includes at least one framing strand and the body lumen has an interior body lumen surface, the framing strand being adapted to exert positive pressure at a plurality of locations on the interior body lumen surface to maintain a position of the at least one target point within the body lumen.

4. The apparatus of claim 1, wherein at least one target point has an associated radiopaque marker to indicate a position of the target point relative to the body lumen in cooperation with an external imaging system.

5. The apparatus of claim 1, wherein the body lumen is at least one of a left atrium, a right atrium, an interatrial septum, an interventricular septum, a peritoneal cavity, a chest cavity, a left atrial appendage, a right atrial appendage, a left pulmonary vein, a blood vessel, a common iliac artery, a subintimal space, a portion of the heart, a gastrointestinal organ, and a genitourinary organ.

6. The apparatus of claim 1, wherein the target pathway is a target lumen.

7. The apparatus of claim 1, wherein the target pathway and framing member are not coaxial with one another.

8. The apparatus of claim 1, wherein the holding mechanism is remotely operable to release the implanted structure within the body lumen when the framing member has achieved a desired deployment position relative to the desired target site.

9. The apparatus of claim 1, wherein the implanted structure is at least one of a ring, a valve, a suture, a stent, a graft, a pledget, an occluder device, an applicator of therapeutic means, and a prosthesis.

10. The apparatus of claim 1, wherein the target pathway is substantially spaced apart from the framing member body.

11. The apparatus of claim 1, including at least one locator structure attached to the framing member to assist with at least one of placement and location of the framing member during operation of the apparatus.

12. The apparatus of claim 1, including at least one attachment assisters to assist with attachment of the implanted structure to the desired target site.

13. The apparatus of claim 1, including the step of assisting with attachment of the implanted structure to the desired target site with at least one attachment assister.

14. The apparatus of claim 1, wherein the holding mechanism is carried substantially at a distalmost extent of the framing member.

\* \* \* \* \*